(12) United States Patent
Park et al.

(10) Patent No.: US 8,796,219 B2
(45) Date of Patent: Aug. 5, 2014

(54) TARGET-ACTIVATED CELL/TISSUE-PENETRATING PEPTIDE FOR DELIVERY OF IMPERMEABLE COMPOUNDS AND USE THEREOF

(75) Inventors: Yoon-Jeong Park, Seoul (KR); Chong-Pyoung Chung, Seoul (KR); Victor C. Yang, Ann Arbor, MI (US)

(73) Assignee: Nano Intelligent Biomedical Engineering Corporation Co. Ltd, Chungcheongbuk-Do (KR)

( * ) Notice: Subject to any disclaimer, the term of this patent is extended or adjusted under 35 U.S.C. 154(b) by 0 days.

(21) Appl. No.: 13/202,317

(22) PCT Filed: Feb. 19, 2010

(86) PCT No.: PCT/KR2010/001033
§ 371 (c)(1),
(2), (4) Date: Sep. 23, 2011

(87) PCT Pub. No.: WO2010/095881
PCT Pub. Date: Aug. 26, 2010

(65) Prior Publication Data
US 2012/0053129 A1    Mar. 1, 2012

(30) Foreign Application Priority Data

Feb. 19, 2009    (KR) .................. 10-2009-0013684

(51) Int. Cl.
| | | |
|---|---|---|
| A61K 38/02 | (2006.01) |
| A61P 35/00 | (2006.01) |
| C07K 19/00 | (2006.01) |
| A61K 47/48 | (2006.01) |
| C07K 14/47 | (2006.01) |
| A61K 38/00 | (2006.01) |

(52) U.S. Cl.
CPC ............ *C07K 14/47* (2013.01); *C07K 2319/10* (2013.01); *A61K 47/48315* (2013.01); *A61K 47/48338* (2013.01); *A61K 38/00* (2013.01)
USPC ......................... 514/19.3; 530/300

(58) Field of Classification Search
CPC .................. A61K 47/48315; A61K 47/48338; A61K 38/00; A61K 51/08; A61K 38/16; A61K 38/1833; A61K 38/191; C07K 14/47; C07K 2319/10; C07K 14/00
See application file for complete search history.

(56) References Cited

U.S. PATENT DOCUMENTS

2005/0107583 A1* 5/2005 Jiang et al. .................. 530/324

FOREIGN PATENT DOCUMENTS

WO    2007095152 A2    8/2007

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Defination of analog, from http://cancerweb.ncl.ac.uk/cgi-bin/omd?query=analog, pp. 1-5, accessed Jul. 7, 2005.*
Moon et al, In vitro assessment of a novel polyrotaxane-based drug delivery system integrated with a cell-penetrating peptide, Journal of Controlled Release, 2007, 124, pp. 43-50.*
Protein crosslinking from http://proteinmods.com/applications/protein-crosslinking/, pp. 1-2, accessed Jun. 17, 2013.*
SMCC, from http://www.piercenet.com/product/smcc, pp. 1-3, accessed Nov. 26, 2013.*
Sulfo-SMCC, from http://www.piercenet.com/product/sulfo-smcc, pp. 1-3, accessed Nov. 26, 2013.*
Wagstaff et al, Protein Transduction: Cell Penetrating Peptides and Their Therapeutic Applications, Current Medicinal Chemistry, 2006, 13, pp. 1371-1387.*
Liu et al, Penetratin, a Potentially Powerful Absorption Enhancer for Noninvasive Intraocular Drug Delivery, Mol. Pharmaceutics, 2014, 11, pp. 1218-1227.*
Eguchi, A., et al., "Efficient siRNA delivery into primary cells by a peptide transduction domain-dsRNA binding domain fusion protein ", "Nature Biotechnology", Jun. 2009, pp. 567-572, vol. 27, No. 6.
Endoh, T., et al., "Cellular siRNA Delivery Mediated by a Cell-Permeant RNA-Binding Protein and Photoinduced RNA Interference", "Bioconjugate Chem.", May 2008, pp. 1017-1024, vol. 19, No. 5.

* cited by examiner

*Primary Examiner* — Julie Ha
*Assistant Examiner* — Li Ni Komatsu
(74) *Attorney, Agent, or Firm* — Hultquist, PLLC; Steven J. Hultquist; Mary B. Grant

(57) ABSTRACT

The present invention relates to a target-activated cell/tissue-penetrating peptide for delivery of impermeable compounds (Target Activated Cell/tissue Translocation peptide for Impermeable Compound Strategy (TACTICS)), and the use thereof, and more particularly to a target-activated cell/tissue-penetrating peptide, which comprises (a) a protein transduction domain (PTD), (b) a masking domain and (c) a spacer having a cleavage site specific for a target cell/tissue enzyme and is provided with target selectivity so as to penetrate specifically into a target tissue, and to a conjugate of the peptide with a drug or drug-containing particles for imaging or therapeutic applications. Because the target-activated cell/tissue-penetrating peptide has target selectivity, the peptide-drug conjugate exhibits maximized imaging and therapeutic effects, and the non-specific distribution of the conjugate in vivo is inhibited, so that the side effects of the conjugate are minimized, the diagnostic effects of the conjugate are maximized, and the conjugate is useful for the treatment of disease.

6 Claims, 4 Drawing Sheets

SEQUENCE LISTING

<160> NUMBER OF SEQ ID NOS: 28

<210> SEQ ID NO 1
<211> LENGTH: 14
<212> TYPE: PRT
<213> ORGANISM: Artificial Sequence
<220> FEATURE:
<223> OTHER INFORMATION: sequence is synthesized

<400> SEQUENCE: 1

Val Ser Arg Arg Arg Arg Arg Gly Gly Arg Arg Arg Arg
1               5                   10

<210> SEQ ID NO 2
<211> LENGTH: 11
<212> TYPE: PRT
<213> ORGANISM: Artificial Sequence
<220> FEATURE:
<223> OTHER INFORMATION: sequence is synthesized

<400> SEQUENCE: 2

Tyr Gly Arg Lys Lys Arg Arg Gln Arg Arg
1               5                   10

<210> SEQ ID NO 3
<211> LENGTH: 16
<212> TYPE: PRT
<213> ORGANISM: Artificial Sequence
<220> FEATURE:
<223> OTHER INFORMATION: sequence is synthesized

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: sequence is synthesized

<400> SEQUENCE: 4

Arg Arg Arg Arg Arg Arg Arg
1               5

<210> SEQ ID NO 5
<211> LENGTH: 10
<212> TYPE: PRT
<213> ORGANISM: Artificial Sequence
<220> FEATURE:
<223> OTHER INFORMATION: sequence is synthesized

<400> SEQUENCE: 5

Lys Lys Lys Lys Lys Lys Lys Lys Lys
1               5                   10

<210> SEQ ID NO 6
<211> LENGTH: 8
<212> TYPE: PRT
<213> ORGANISM: Artificial Sequence
<220> FEATURE:
<223> OTHER INFORMATION: sequence is synthesized

<400> SEQUENCE: 6

Cys His Ser Ser Lys Leu Gln Gly
1               5

```
<210> SEQ ID NO 7
<211> LENGTH: 8
<212> TYPE: PRT
<213> ORGANISM: Artificial Sequence
<220> FEATURE:
<223> OTHER INFORMATION: sequence is synthesized

<400> SEQUENCE: 7

Leu Arg Leu Ser Ser Tyr Tyr Met
1               5

<210> SEQ ID NO 8
<211> LENGTH: 6
<212> TYPE: PRT
<213> ORGANISM: Artificial Sequence
<220> FEATURE:
<223> OTHER INFORMATION: sequence is synthesized

<400> SEQUENCE: 8

Ser Ser Gln Pro Trp Gln
1               5

<210> SEQ ID NO 9
<211> LENGTH: 6
<212> TYPE: PRT
<213> ORGANISM: Artificial Sequence
<220> FEATURE:
<223> OTHER INFORMATION: sequence is synthesized

<400> SEQUENCE: 9

Arg Arg Phe Leu Cys Gly
1               5

<210> SEQ ID NO 10
<211> LENGTH: 6
<212> TYPE: PRT
<213> ORGANISM: Artificial Sequence
<220> FEATURE:
<223> OTHER INFORMATION: sequence is synthesized

<400> SEQUENCE: 10

Thr His Asp Asn Asp Leu
1               5

<210> SEQ ID NO 11
<211> LENGTH: 5
<212> TYPE: PRT
<213> ORGANISM: Artificial Sequence
<220> FEATURE:
<223> OTHER INFORMATION: sequence is synthesized

<400> SEQUENCE: 11

Val Arg Pro Ile Glu
1               5

<210> SEQ ID NO 12
<211> LENGTH: 6
<212> TYPE: PRT
<213> ORGANISM: Artificial Sequence
<220> FEATURE:
<223> OTHER INFORMATION: sequence is synthesized

<400> SEQUENCE: 12

Val Ser Gly Trp Gly Thr
1               5
```

```
<210> SEQ ID NO 13
<211> LENGTH: 4
<212> TYPE: PRT
<213> ORGANISM: Artificial Sequence
<220> FEATURE:
<223> OTHER INFORMATION: sequence is synthesized

<400> SEQUENCE: 13

Tyr Pro Ala Ser
1

<210> SEQ ID NO 14
<211> LENGTH: 6
<212> TYPE: PRT
<213> ORGANISM: Artificial Sequence
<220> FEATURE:
<223> OTHER INFORMATION: sequence is synthesized

<400> SEQUENCE: 14

Thr Ile Thr Pro Gly Met
1               5

<210> SEQ ID NO 15
<211> LENGTH: 6
<212> TYPE: PRT
<213> ORGANISM: Artificial
<220> FEATURE:
<223> OTHER INFORMATION: spacer

<400> SEQUENCE: 15

Gln Gly Arg Ala Met Cys
1               5

<210> SEQ ID NO 16
<211> LENGTH: 6
<212> TYPE: PRT
<213> ORGANISM: Artificial Sequence
<220> FEATURE:
<223> OTHER INFORMATION: sequence is synthesized

<400> SEQUENCE: 16

Gly Pro Arg Ala Met Cys
1               5

<210> SEQ ID NO 17
<211> LENGTH: 6
<212> TYPE: PRT
<213> ORGANISM: Artificial Sequence
<220> FEATURE:
<223> OTHER INFORMATION: sequence is synthesized

<400> SEQUENCE: 17

Gln Arg Arg Ala Met Cys
1               5

<210> SEQ ID NO 18
<211> LENGTH: 6
<212> TYPE: PRT
<213> ORGANISM: Artificial Sequence
<220> FEATURE:
<223> OTHER INFORMATION: sequence is synthesized

<400> SEQUENCE: 18

Gly Gly Arg Ala Met Cys
1               5
```

```
<210> SEQ ID NO 19
<211> LENGTH: 6
<212> TYPE: PRT
<213> ORGANISM: Artificial
<220> FEATURE:
<223> OTHER INFORMATION: spacer

<400> SEQUENCE: 19

Val Leu Lys Ala Met Cys
1               5

<210> SEQ ID NO 20
<211> LENGTH: 6
<212> TYPE: PRT
<213> ORGANISM: Artificial Sequence
<220> FEATURE:
<223> OTHER INFORMATION: sequence is synthesized

<400> SEQUENCE: 20

Leu Gly Arg Ala Met Cys
1               5

<210> SEQ ID NO 21
<211> LENGTH: 6
<212> TYPE: PRT
<213> ORGANISM: Artificial Sequence
<220> FEATURE:
<223> OTHER INFORMATION: sequence is synthesized

<400> SEQUENCE: 21

Gln Ala Arg Ala Met Cys
1               5

<210> SEQ ID NO 22
<211> LENGTH: 6
<212> TYPE: PRT
<213> ORGANISM: Artificial Sequence
<220> FEATURE:
<223> OTHER INFORMATION: sequence is synthesized

<400> SEQUENCE: 22

Val Pro Arg Ala Met Cys
1               5

<210> SEQ ID NO 23
<211> LENGTH: 6
<212> TYPE: PRT
<213> ORGANISM: Artificial Sequence
<220> FEATURE:
<223> OTHER INFORMATION: sequence is synthesized

<400> SEQUENCE: 23

Pro Phe Arg Ala Met Cys
1               5

<210> SEQ ID NO 24
<211> LENGTH: 6
<212> TYPE: PRT
<213> ORGANISM: Artificial Sequence
<220> FEATURE:
<223> OTHER INFORMATION: sequence is synthesized

<400> SEQUENCE: 24

Phe Ser Arg Ala Met Cys
1               5

<210> SEQ ID NO 25
```

```
<211> LENGTH: 6
<212> TYPE: PRT
<213> ORGANISM: Artificial Sequence
<220> FEATURE:
<223> OTHER INFORMATION: sequence is synthesized

<400> SEQUENCE: 25

Pro Leu Gly Leu Ala Gly
1               5

<210> SEQ ID NO 26
<211> LENGTH: 5
<212> TYPE: PRT
<213> ORGANISM: Artificial Sequence
<220> FEATURE:
<223> OTHER INFORMATION: sequence is synthesized

<400> SEQUENCE: 26

Ser Gly Arg Ser Ala
1               5

<210> SEQ ID NO 27
<211> LENGTH: 7
<212> TYPE: PRT
<213> ORGANISM: Artificial Sequence
<220> FEATURE:
<223> OTHER INFORMATION: sequence is synthesized

<400> SEQUENCE: 27

Glu Glu Glu Glu Glu Glu Glu
1               5

<210> SEQ ID NO 28
<211> LENGTH: 27
<212> TYPE: PRT
<213> ORGANISM: Artificial Sequence
<220> FEATURE:
<223> OTHER INFORMATION: sequence is synthesized

<400> SEQUENCE: 28

Glu Glu Glu Glu Glu Glu Glu Pro Leu Gly Leu Ala Gly Val Ser Arg
1               5                   10                  15

Arg Arg Arg Arg Arg Gly Gly Arg Arg Arg Arg
                20                  25
```

TARGET-ACTIVATED CELL/TISSUE-PENETRATING PEPTIDE FOR DELIVERY OF IMPERMEABLE COMPOUNDS AND USE THEREOF

CROSS-REFERENCE TO RELATED APPLICATIONS

This application is a U.S. national phase under the provisions of 35 U.S.C. §371 of International Patent Application No. PCT/KR10/01033 filed Feb. 19, 2010, claiming the priority of Korean Patent Application No. 10-2009-0013684 filed Feb. 19, 2009. The disclosures of such international patent application and Korean priority patent application are hereby incorporated herein by reference in their respective entireties, for all purposes.

TECHNICAL FIELD

The present invention relates to a target-activated cell/tissue-penetrating peptide for delivery of impermeable compounds, and the use thereof, and more particularly to a target-activated cell/tissue-penetrating peptide, which is provided with target selectivity so as to introduce a drug or drug-containing particles specifically into a target cell/tissue, and to a conjugate of the peptide with a drug or drug-containing particles.

BACKGROUND ART

In the field of the diagnosis or treatment of disease, attempts have been made for a long time to cause a desired substance to act selectively in a target cell or tissue while remaining only therein.

Particularly, in the field of the treatment of tumors or the diagnosis or treatment of osteoarthritis and brain disease, many studies on the proteins or small molecules present specifically in target lesions have been conducted. As a result, many types of materials specifically present in target lesions have been identified while studies on the use thereof for therapeutic purposes have also been actively conducted. For example, it has appeared that, in prostate cancer, prostate specific antigen (PSA) is largely present, and in other tumor tissues, matrix metalloprotease (MMP) is more highly expressed than in normal tissue. Thus, such identified materials have been used as targets in the research and treatment of disease. However, if materials which are used for the diagnosis and treatment of diseases do not act specifically in such targets, problems of side effects or low image quality, which are caused by the non-specific distribution of the materials, will arise. For this reason, development of formulations which remain or act only in targets has been requested.

Generally, only some small molecules can enter the cytoplasm or nucleus of live cells through the cell membrane at a very low ratio, whereas large molecules cannot enter cells. However, because most materials, which are prepared for therapeutic, preventive or diagnostic purposes and the effective amount of which should be delivered into cells, are large molecules or macromolecules, methods of delivering biologically active macromolecules into cells without damaging the cells both in vivo and ex vivo have been demanded.

As a result of studies conducted to satisfy this demand, protein transduction domains (PTDs) have been suggested, and among them, TAT protein which is the transcription factor of human immunodeficiency virus-1 (HIV-1) has been most frequently studied. It was found that the TAT protein is more effective in passing through the cell membrane when it is composed of amino acids 47 to 57 (YGRKKRRQRRR), on which positively charged amino acids are concentrated, compared to when it is in a full-length form consisting of 86 amino acids (Fawell, S. et al., *Proc. Natl. Acad. Sci. USA*, 91:664, 1994). Other examples of PTDs include a peptide having a sequence of amino acids 267 to 300 of the VP22 protein of Herpes Simplex Virus type 1 (HSV-1) (Elliott G. et al., Cell 88:223-233, 1997), a peptide having a sequence of amino acids 84 to 92 of the UL-56 protein of HSV-2 (GenBank code:D1047[gi:221784]), and a peptide having a sequence of amino acids 339 to 355 of the Antennapedia (ANTP) protein of *Drosophila* sp. (Schwarze, S. R. et al., *Trends. Pharmacol. Sci.*, 21:45, 2000). In addition, artificial peptides consisting of positively charged amino acids also showed the effect of delivering drugs (Laus, R. et al., *Nature. Biotechnol.*, 18:1269, 2000).

Recently, the present inventors reported the preparation of a low-molecular-weight protamine (LMWP) and the cell-penetrating activity thereof, in which the low-molecular-weight protamine (LMWP) has a peptide sequence similar to TAT, serves as a protein transduction domain and contains a large amount of cationic amino acids such as arginine. Particularly, the LMWP is a naturally occurring cationic peptide from protamine and is advantageous in that it presents no toxicity concerns and can be produced in large amounts (Park, Y. J. et al., *J. Gene. Med.*, 700, 2003). However, this peptide is required to be additionally provided with target selectivity so that it is used for selective imaging, diagnostic or therapeutic purposes.

Accordingly, the present inventors have extensively made efforts to develop a method which can minimize problems of side effects or low image quality, attributable to the non-specific distribution of existing agents for the diagnosis or treatment of diseases, and which can effectively deliver a diagnostic or disease-treating agent specifically into a target cell. As a result, the present inventors have prepared a target-activated cell/tissue-penetrating peptide comprising a protein transduction domain (PTD), a spacer having a cleavage site specific for a target tissue enzyme, and a masking domain ionically bonded to the protein transduction domain (PTD), and have found that, when the prepared peptide is used as a conjugate with a drug, the drug is introduced specifically into a target cell/tissue, thereby completing the present invention.

DISCLOSURE OF INVENTION

It is an object of the present invention to provide a target-activated cell/tissue-penetrating peptide for delivery of impermeable compounds, which serves to introduce a drug or drug-containing particles specifically into a target cell/tissue, and a conjugate of the peptide with either a drug or drug-containing particles.

Another object of the present invention is to provide a pharmaceutical composition for diagnosis and treatment of diseases, including cancer and inflammation, the composition comprising a conjugate of said target-activated cell/tissue-penetrating peptide with a drug.

To achieve the above objects, the present invention provides a target-activated cell/tissue-penetrating peptide for delivery of impermeable compounds, which includes:

(a) a protein transduction domain (PTD);
(b) a masking domain ionically bonded with the protein transduction domain (PTD); and
(c) a spacer connecting the protein transduction domain (PTD) with the masking domain and having a cleavage domain specific for a target cell/tissue enzyme.

In the present invention, the protein transduction domain (PTD) may consist of D-type or L-type amino acids, and 70-80% of the protein transduction domain (PTD) may consist of any one or more amino acids selected from the group consisting of arginine, lysine and histidine.

In the present invention, the masking domain ionically bonded with the protein transduction domain (PTD) may consist of D-type or L-type amino acids, and 70-100% of the masking domain may consist of anionic amino acids. Herein, the anionic amino acids may include glutamic acid or aspartic acid, and preferably, the masking domain may consist of 4-8 amino acids.

In the present invention, the spacer may have a site which is cleaved by any one enzyme selected from the group consisting of prostate cancer cell surface enzyme, Kallikrein 14 (KLK14), Cathepsin, and matrix metalloprotease (MMP).

The present invention also provides a target-activated cell/tissue-penetrating peptide-drug conjugate, in which the target-activated cell/tissue-penetrating peptide is conjugated with a drug or drug-containing particles.

In the present invention, the drug or the drug-containing particles may be conjugated with the protein transduction domain (PTD) of the target-activated cell/tissue-penetrating peptide. Preferably, the protein transduction domain (PTD) may be linked with the drug or the drug-containing particles by cystein.

In the present invention, the drug may be selected from the group consisting of anticancer agents, anticancer proteins, anti-inflammatory agents, anti-inflammatory proteins, immune enhancing proteins, bone resorption inhibitors, antisense oligonucleotides targeting the RNA of tumor or inflammatory disease proteins, and siRNAs targeting the RNA of tumor or inflammatory disease proteins.

The present invention also provides a pharmaceutical composition for diagnosis and treatment of disease, which comprises said target-activated cell/tissue-penetrating peptide-drug conjugate. Specifically, a pharmaceutical composition for treatment of, for example, cancer disease, may be provided.

The present invention also provides a method for treating cancer disease, comprising administering said target-activated cell/tissue-penetrating peptide-drug conjugate.

The present invention also provides the use of said target-activated cell/tissue-penetrating peptide-drug conjugate for treatment of cancer.

Other features and embodiments of the present invention will be more apparent from the following detailed descriptions and the appended claims.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows.

As used herein, the term "protein transduction domain (PTD)" refers to a penetrating peptide that can introduce a drug or drug-containing particles into the cytoplasm or nucleus of a cell. It means that the protein transduction domain (PTD) forms a covalent bond with oligonucleotides, peptides, proteins, oligosaccharides, polysaccharides or nanoparticles so that it can introduce these materials into cells without requiring a separate receptor, delivery system or energy.

As used herein, the term "target cell/tissue" refers to a cell and tissue, particularly an in vivo or ex vivo cell, into which a drug or drug-containing particles are delivered by the target-activated cell/tissue-penetrating peptide. Specifically, the term "target cell/tissue" is means to include in vivo cells, that is, the cells of the organ or tissue of live animals or humans, or microorganisms found in live animals or humans. Also, the term "target cell/tissue" is means to include ex vivo cells, that is, cultured animal cells, human cells or microorganisms.

In one aspect, the present invention is directed to a target-activated cell/tissue-penetrating peptide for delivery of impermeable compounds, which includes:
(a) a protein transduction domain (PTD);
(b) a masking domain ionically bonded with the protein transduction domain (PTD); and
(c) a spacer connecting the protein transduction domain (PTD) with the masking domain and having a cleavage domain specific for a target cell/tissue enzyme.

Figure 1:
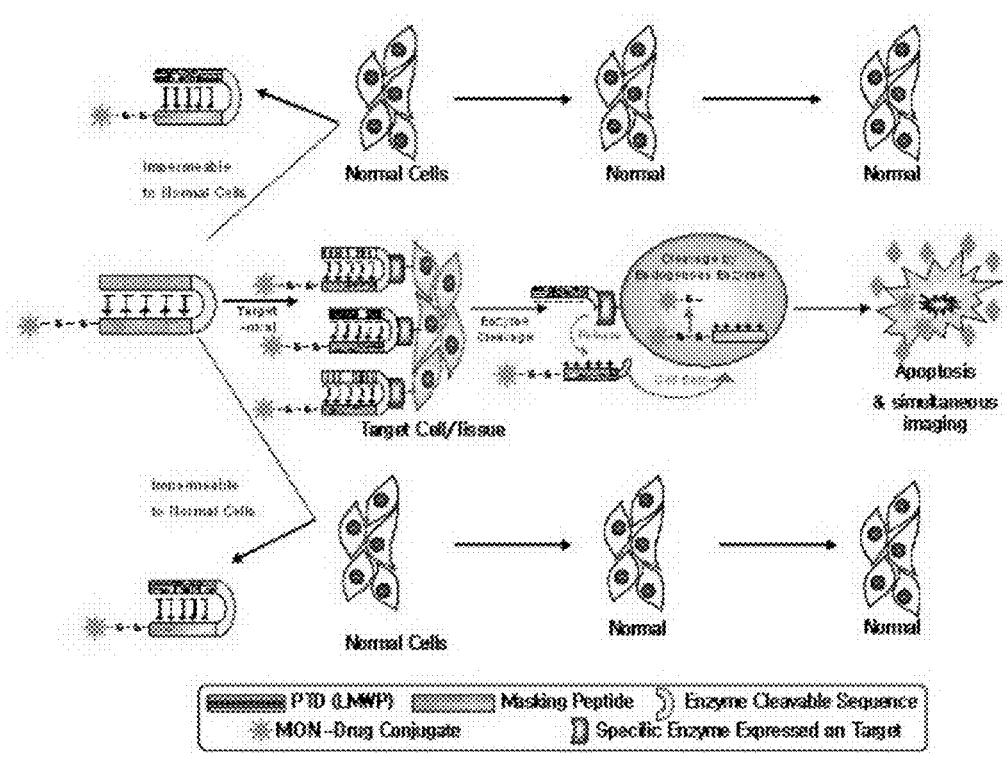
FIG. 1 is a schematic diagram showing the mechanism of a target-activated cell/tissue-penetrating peptide-drug conjugate according to the present invention.

The present invention relates to a technique for drug delivery into a cell/tissue, in which a target-activated cell/tissue-penetrating peptide is prepared so that a drug or drug-containing particles (e.g., drug-containing nanomagnetic particles), conjugated with the peptide, can be introduced only into a target cell/tissue. As shown in FIG. 1, a drug or drug-containing nanoparticles which are to be introduced are chemically conjugated with the peptide, and then treated in in vivo and in vitro in an aqueous solution so that they can be introduced only into target cells without being introduced into non-target cells. In other words, the drug can be introduced directly into cells without an endocytosis process that is an existing intracellular delivery process.

The target-activated cell/tissue-penetrating peptide according to the present invention can be prepared by chemical synthesis using a peptide synthesis system. Specifically, a spacer and a masking domain can be sequentially chemically synthesized in the C-terminal region of a protein transduction domain (PTD) having cell-penetrating activity so that the peptide can be synthesized in the order of the N-terminal region, the protein transduction domain, the spacer, the masking domain and the C-terminal region. Alternatively, the peptide may also be synthesized in the order of the N-terminal region, the masking domain, the spacer, the protein transduction domain, and the C-terminal region.

In the present invention, 70-80% of the protein transduction domain (PTD) may consist of any one or more amino acids selected from the group consisting of arginine, lysine and histidine. Also, the amino acids of the protein transduction domain (PTD) may be L-type or D-type amino acids in view of stability in vivo.

Examples of a protein transduction domain (PTD) having cell-penetrating activity, which can be used in the present invention, include, in addition to the transduction domain LMWP (SEQ ID NO 1: VSRRRRRRGGRRRR) discovered by the present inventors, cationic protein transduction domain peptides, 70-80% or more of the amino acids of which consist of arginine, lysine or histidine. Preferred examples of the cationic protein transduction domain peptides that may be used in the present invention include TAT (SEQ ID NO 2: YGRKKRRQRRR), Penetratin (SEQ ID NO: 3: RQIKIWFQNRRMKWKK), polyarginine (SEQ ID NO 4: RRRRRRR), polylysine (SEQ ID NO 5: KKKKKKKKKK), a protamine fragment, and Antennapedia (ANTP). In addition to the above-described peptides, other peptides or peptide analogs may also be used in the present invention, as long as they can permeate the cell membrane.

In the present invention, 70-100% of the masking domain ionically bonded with the protein transduction domain (PTD) may consist of anionic amino acids. In addition, the amino acids of the masking domain may be L-type or D-type amino acids in view of stability in vivo. Herein, the anionic amino acids may include glutamic acid or aspartic acid, and preferably, the masking domain may consist of 4-8 amino acids.

In the present invention, the spacer may have a site which is cleaved by any one enzyme selected from the group consisting of prostate cancer cell surface enzyme, Kallikrein 14 (KLK14), Cathepsin, and matrix metalloprotease (MMP).

Herein, the spacer includes any one selected from the group consisting of SEQ ID NO: 6 (CHSSKLQG), SEQ ID NO: 7 (LRLSSYYM), SEQ ID NO: 8 (SSQPWQ), SEQ ID NO: 9 (RRFLCG), SEQ ID NO: 10 (THDNDL), SEQ ID NO: 11 (VRPIE), SEQ ID NO: 12 (VSGWGT), SEQ ID NO: 13 (YPAS), SEQ ID NO: 14 (TITPGM), SEQ ID NO: 15 (QGRAMC), SEQ ID NO: 16 (GPRAMC), SEQ ID NO: 17 (QRRAMC), SEQ ID NO: 18 (GGRAMC), SEQ ID NO: 19 (VLKAMC), SEQ ID NO: 20 (LGRAMC), SEQ ID NO: 21 (QARAMC), SEQ ID NO: 22 (VPRAMC), SEQ ID NO: 23 (PFRAMC), SEQ ID NO: 24 (FSRAMC), SEQ ID NO: 25 (PLGLAG) and SEQ ID NO: 26 (SGRSA). The amino acids of the spacer may be L-type amino acids for the sake of smooth cleaving of the spacer by enzyme.

In another aspect, the present invention is also directed to a target-activated cell/tissue-penetrating peptide-drug conjugate, in which the target-activated cell/tissue-penetrating peptide is conjugated with a drug or drug-containing particles.

The target-activated cell/tissue-penetrating peptide is covalently bonded to a drug or drug-containing particles to provide a target-activated cell/tissue-penetrating peptide-drug conjugate, in which the drug or the drug-containing particles can be covalently bonded to the N- or C-terminal region of the protein transduction domain (PTD) of the target-activated cell/tissue-penetrating peptide. Preferably, cystein additionally attached to the terminal region of the protein transduction domain (PTD) may be used in the chemical bonding.

Also, the peptide-drug conjugate can be prepared by using a crosslinking agent to induce chemical bonding. When the crosslinking agent is used to induce chemical bonding, the formation of the conjugate by the crosslinking agent is facilitated, because the N-terminal region of the protein transduction domain (PTD) peptide, that is, the protein transduction domain (PTD), has a free amino group. Examples of a crosslinking agent that may be used in the present invention include, but are not limited to, 1,4-bis-maleimidobutane (BMB), 1,11-bis-maleimidotetraethyleneglycol (BM[PEO]-4), 1-ethyl-3-[3-dimethyl aminopropyl]carbodiimide hydrochloride (EDC), succinimidyl-4-[N-maleimidomethylcyclohexane-1-carboxy-[6-amidocaproate]] (SMCC) and its sulfonate (sulfo-SMCC), succinimidyl 6-[3-(2-pyridyldithio)-ropionamido]hexanoate (SPDP) and its sulfonate (sulfo-SPDP), m-maleimidobenzoyl-N-hydroxysuccinimide ester (MBS) and its sulfonate (sulfo-MBS), and succimidyl[4-(p-maleimidophenyl) butyrate] (SMPB) and its sulfonate (sulfo-SMPB). If the cell-penetrating peptide is bonded to a drug or drug-containing particles by an S—S bond, the drug can be disassociated from the cell-penetrating peptide by, for example, reductase present in cells. When this method is used, a drug, a protein or other nanoparticles can be introduced into cells in an easy and convenient manner without the time-consuming construction of a recombinant vector, thus easily achieving the desired therapeutic effect.

Examples of a drug that may be used in the present invention include anticancer agents, anti-inflammatory agents, bone resorption inhibitors, anticancer proteins, anti-inflammatory proteins, immune enhancing proteins, anticancer and anti-inflammatory siRNAs, oligonucleotides, and nanomagnetic particles containing one or more thereof. As used herein, the term "siRNA" means RNA silencing the expression of a target RNA, in which the target RNA is mRNA transcribed from disease-causing genes, particularly tumor- or inflammation-causing genes. Examples of an oncogene include, but are not limited to, vascular endothelial growth factor (VEGF) genes.

Herein, the tumor- or inflammation-causing protein may be selected from the group consisting of vascular endothelial growth factor (VEGF), B-cell leukemia/lymphoma 2 (BCL2), epidermal growth factor receptor (EGFR), human epidermal growth factor receptor 2 (HER2), Janus kinase (JAN), and phosphatidylinositol-3-kinase/Akt kinase (PI3-K/AKT).

In still another aspect, the present invention is also directed to a pharmaceutical composition for diagnosis and treatment of disease, which comprises said target-activated cell/tissue-penetrating peptide-drug conjugate. Specifically, a pharmaceutical composition for treatment of, for example, cancer disease, may be provided.

In one Example of the present invention, the target-activated cell/tissue-penetrating peptide according to the present invention was labeled with the fluorescence marker FITC and applied to normal cells and tumor cells, and as a result, it was observed that the fluorescence intensity of the tumor cells increased, whereas the fluorescence intensity of the normal cells was the same as that before application of the penetrating peptide. This suggests that the spacer is cleaved by the enzyme on the tumor cell surface, and thus the fluorescence-labeled target-activated cell/tissue-penetrating peptide is dissociated and introduced into the tumor cells, whereas the penetration activity of the peptide in the normal cells is not exhibited, because the enzyme present on the normal cell surface is insignificant so that the spacer is difficult to cleave. Also, in another Example of the present invention, a tumor suppressor protein was bound to the terminal region of this peptide, and as a result, it was shown that the tumor suppressor protein did not influence the growth of normal cells, whereas it inhibited the growth of tumor cells. In addition, an MTT assay was performed to measure the effective inhibitory concentration (IC50) of the target-activated cell/tissue-penetrating peptide-drug conjugate according to the present invention, and as a result, the peptide-drug conjugate showed cytotoxicity even at a low concentration of $5 \times 10^{-9}$ M.

The pharmaceutical composition of the present invention can be administered together with a pharmaceutically acceptable carrier. For oral administration, a binding agent, a lubricant, a disintegrant, an excipient, a solubilizer, a dispersing agent, a stabilizer, a suspending agent, a pigment and a flavor may be used. In the case of injectable formulations, a buffer, a preservative, an analgesic agent, a solubilizer, an isotonic agent and a stabilizer may be used, and in the case of topical formulations, a base, an excipient, a lubricant and a preservative may be used. The pharmaceutical composition of the present invention may be formulated in various forms by mixing with pharmaceutically acceptable carriers. For example, for oral administration, the composition may be formulated in the form of tablets, troches, capsules, elixirs, suspensions, syrups, and wafers, and for injectable formulations, the composition may be prepared into a single dosage ampoule or a multiple dosage form.

The composition of the present invention may be administered in a therapeutically or preventively effective amount. The dose of the composition of the present invention can vary depending on various factors, including the patient's age, sex, weight and drug sensitivity, the kind and severity of disease, the type of current therapy, the mode of administration, a particular target cell, and the like, and can be easily determined by a person skilled in the art. The composition of the present invention may be administered in combination with other therapeutic agents and may be administered sequentially or simultaneously with other therapeutic agents. Also, the composition may be administered in a single or multiple dosage form. It is important to administer the composition in the minimum amount that can exhibit the maximum effect without causing side effects, in view of all the above-described factors, and this amount can be easily determined by a person skilled in the art.

As used herein, the term "administration" means introducing a given material into a patient by any appropriate method. The composition of the present invention may be administered by any general route, as long as it can reach a target tissue. Specifically, the composition of the present invention may be administered intraperitoneally, intravenously, intramuscularly, subcutaneously, intradermally, orally, locally, intranasally, intrapulmonarily or intrarectally, but is not limited thereto. In addition, the pharmaceutical composition of the present invention may be administered using any system capable of delivering the active ingredient to target cells.

EXAMPLES

In the following examples, only the anticancer protein gelonin was illustrated as a drug. However, it will be obvious to those skilled in the art that the use of other anticancer proteins, anti-oncogenic antisense oligonucleotides, siRNAs, or particles containing one or more thereof can have the same or similar effect on the treatment of tumors and that the use of anti-inflammatory substances, anti-inflammatory proteins or the like as anti-inflammatory drugs can provide anti-inflammatory effects.

Example 1

Preparation of Target-Activated Cell/Tissue-Penetrating Peptide

A target-activated cell/tissue-penetrating peptide was synthesized by an F-moc solid phase method using a peptide synthesis system such that it contains, in order from the N-terminal region, a masking domain (EEEEEEE; SEQ ID NO: 27), a spacer (PLGLAG; SEQ ID NO: 25) which is cleaved by MMP, and LMWP as a protein transduction domain (PTD).

$NH_2$-EEEEEEEPLGLAG-VSRRRRRRGGRRRR-C-COO$NH_2$ (SEQ ID NO: 28)

The synthesized peptide sequence was cleaved from resin, washed and freeze-dried, after which it was purified by liquid chromatography. The molecular weight of the purified peptide was measured by MALDI analysis.

Example 2

Preparation of Target-Activated Cell/Tissue-Penetrating Peptide-Drug Conjugate

The target-activated cell/tissue-penetrating peptide prepared in Example 1 contained cystein, and thus had a free sulfhydryl group. Thus, the cystein was used as a crosslinking agent to induce chemical bonding with the anticancer protein gelonin.

The surface modification of gelonin was performed by attaching a thiol (—SH) group to the carboxyl group on the surface. One thiol (—SH) molecule of the particle surface was allowed to react with 10 thiol (—SH) molecules of the peptide at 4° C. for 12 hours, after which unreacted molecules were removed by ultrafiltration. Then, the remaining material was freeze-dried, thus obtaining a target-activated cell/tissue-penetrating peptide-gelonin conjugate.

Example 3

Tumor Cell-Penetrating Ability Of Target-Activated Cell/Tissue-Penetrating Peptide In order to examine the cell-penetrating ability of the target-activated cell/tissue-penetrating peptide prepared in Example 1, the C-terminal region of the prepared peptide was labeled with the fluorescence marker FITC, and the fluorescence-labeled peptide was inoculated into each of a normal cell line (ATCC) and a tumor cell line (CT-26, KCLB (Korea cell line bank) 80009).

Figure 2:
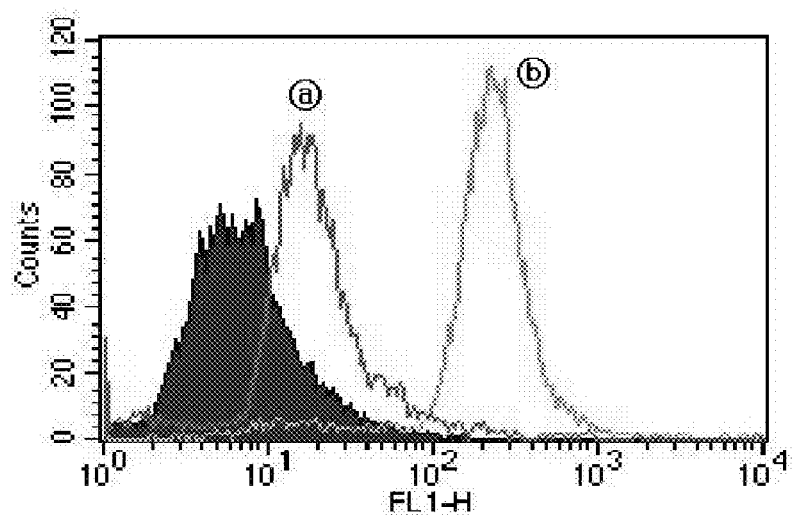
FIG. 2 shows the results of FACS analysis conducted to measure the fluorescence intensities of a normal cell line (ⓐ) and a tumor cell line (ⓑ) after treatment with a fluorescence-labeled target-activated cell/tissue-penetrating peptide.

1 hour after the inoculation, the fluorescence intensities of the cell lines were measured using FACS, and the results of the measurement are shown in FIG. 2. As can be seen therein, an increase in the fluorescence intensity of the tumor cells was observed. In FIG. 2, "(a)" indicates the fluorescence intensity of the normal cell line, and "(b)" indicates the fluorescence intensity of the tumor cell line.

Figure 3:
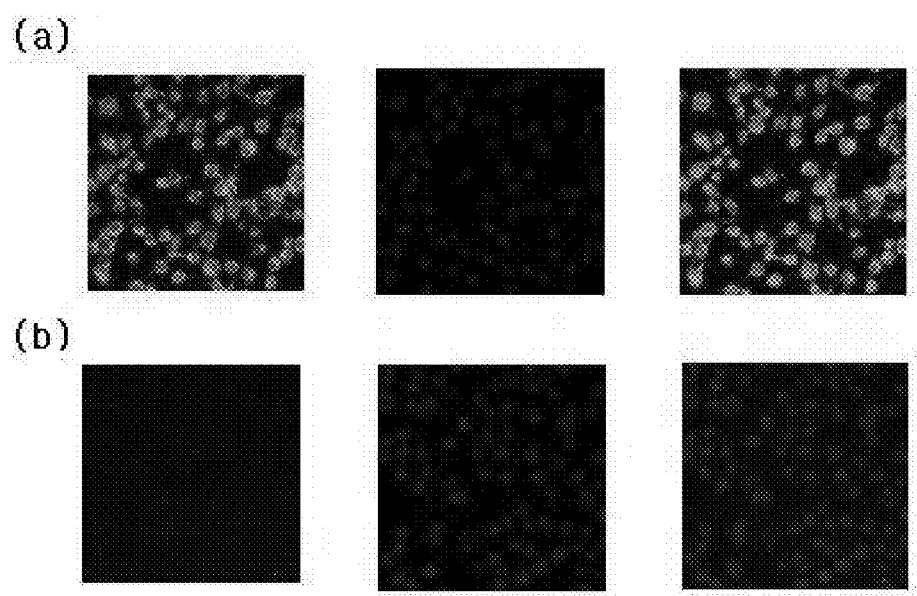
FIG. 3 is a set of confocal micrographs of a tumor cell line group (a) and a normal cell line group (b), observed after treatment with a fluorescence-labeled target-activated cell/tissue-penetrating peptide. In each of 3(a) and 3(b) the left figure shows fluorescence-labeled peptide at 488 nm, the center figure shows the result at 380 nm after the cell nuclei were stained with Hoechst 33342 (Invitrogen, USA) and the right figure shows the cell-penetrating ability of the target-activated cell/tissue-penetrating peptide by integrating the first and second figures.

Also, whether the peptide penetrated into the cells was observed by a confocal laser scanning microscope. In order to demonstrate that stained portions are cells, the cell nuclei was stained with Hoechst 33342 (5 μg/Ml), after which the cells were fixed with a 10% neutral formalin solution. The results of the observation are shown in FIG. 3. As can be seen in FIG. 3, the fluorescence-labeled peptide was observed in the tumor cell line, whereas it was not observed in the normal cell line. In FIG. 3, "(a)" indicates the cell penetration of the peptide in the tumor cell line group, and "(b)" indicates the cell penetration of the peptide in the normal cell line group.

From the above experimental results, it can be seen that the spacer having a cleavage site sequence (PLGLAG; SEQ ID NO: 25) specific for the tumor cell surface enzyme (MMP) was cleaved by the action of the enzyme on the tumor cell surface, while the masking domain (EEEEEEE: SEQ ID NO: 27) ionically bonded to the protein transduction domain (PTD) of the target-activated cell/tissue-penetrating peptide was dissociated from the peptide, so that the protein transduction domain (PTD) was smoothly introduced into the cells. On the other hand, in the case of the normal cells, the cleavage of the spacer by the enzyme did not occur, indicating that the introduction of the peptide into the normal cells was inhibited.

Example 4

Figure 4:
FIG. 4 is a set of confocal micrographs showing the fluorescence intensities of a normal cell line group (ⓐ) and a tumor cell line group (ⓑ), observed after treatment with a target-activated cell/tissue-penetrating peptide-gelonin conjugate. In each of 4(a) and 4(b), the left figure shows the peptide labeled with the fluorescence marker FITC, and the right figure shows the result at 380 nm after the cell nuclei were stained with Hoechst 33342 (Invitrogen, USA).

Tumor Cell-Penetrating Ability of Target-Activated Cell/Tissue-Penetrating Peptide-Anticancer Protein Conjugate The target-activated cell/tissue-penetrating peptide-anticancer protein conjugate prepared in Example 2 above was inoculated into each of a normal cell line (ATCC) and a tumor cell line (CT-26, KCLB (Korea cell line bank) 80009). 1 hour after the inoculation, the penetration of the peptide-gelonin conjugate into the cells was observed by a confocal laser scanning microscope (FIG. 4). In order to demonstrate the stained portions are cells, the cell nuclei were stained with Hoechst 33342 (5 μg/Ml), and then the cells were fixed with 10% neutral formalin solution.

Figure 5:
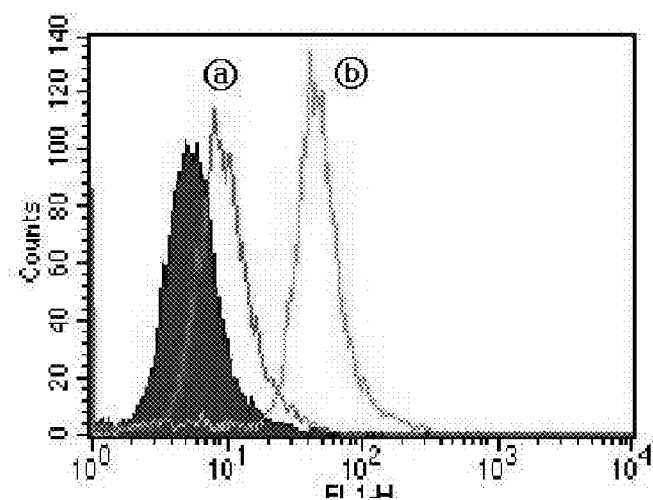
FIG. 5 is a set of photographs showing the results of FACS analysis conducted to measure the fluorescence intensities of a normal cell line (ⓐ) and a tumor cell line (ⓑ) after treatment with a target-activated cell/tissue-penetrating peptide-gelonin conjugate.

The results of the observation are shown in FIG. 5. As can be seen therein, the fluorescence intensity of the tumor cell line increased when treated with the peptide-gelonin conjugate. Also, under the confocal laser scanning microscope, the fluorescence-labeled conjugate was observed in the tumor cell line, whereas it was not observed in the normal cell line.

From the above experimental results, it can be seen that the spacer was cleaved by the action of the enzyme on the tumor cell surface, while the masking domain ionically bonded to the protein transduction domain (PTD) of the target-activated cell/tissue-penetrating peptide was dissociated from the peptide, so that the protein transduction domain (PTD) was smoothly introduced into the cells. On the other hand, in the case of the normal cells, the cleavage of the spacer by the enzyme did not occur, indicating that the introduction of the peptide into the normal cells was inhibited.

Example 5

Measurement of Effective Inhibitory Concentration (IC50) of Target-Activated Cell/Tissue-Penetrating Peptide-Anticancer Protein Conjugate In order to the effective inhibitory concentration (IC50) of the target-activated cell/tissue-penetrating peptide-drug conjugate prepared in Example 2, an MTT assay was performed. The MTT assay is an assay using the ability of mitochondria that reduces a yellow water-soluble substrate, MTT tetrazolium, to a purple water-insoluble MTT formazan by the action of dehydrogenase.

Normal mouse fibroblasts and mouse colon cancer cells (CT-26, KCLB (Korea cell line bank) 80009) were cultured, and then each of the normal cell group and the cancer cell group was treated with varying concentrations of the target-activated cell/tissue-penetrating peptide-gelonin conjugate. After 24 hours, MTT reagent, 3-(4,5-dimethylthiazol-2-ly)-2,5-diphenyl tetrazolium bromide (MTT), was added to each cell group, which was then cultured at 37° C. for 4 hours. Then, the medium was removed, the same amount of DMSO as that of MTT reagent was added to each cell group, and the absorbance of the cell at 540 nm was measured, thereby determining the survival rate of the cells.

Figure 6:
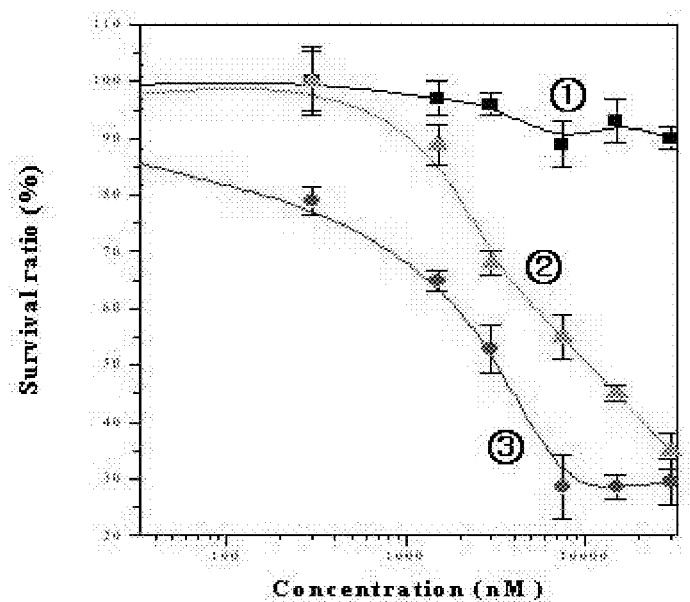
FIG. 6 is a graph showing the survival rates of a normal cell group (①) and a tumor cell group (② and ③) as a function of the treatment concentration of a target-activated cell/tissue-penetrating peptide-gelonin conjugate. ② and ③ indicate the results of two experiments on the survival rate of the tumor cell group.

The results of the measurement are shown in FIG. 6. As can be seen therein, the applied peptide-anticancer protein conjugate showed no cytotoxicity in the normal cell group, whereas it showed significant cytotoxicity in the tumor cell group. The effective inhibitory concentration (IC50) of the peptide-anticancer protein conjugate was measured to be about $5 \times 10^{-9}$ M. In FIG. 6, "(1)" indicates the survival rate of the normal cell group, and "(2)" and "(3)" indicate the results of two experiments on the survival rate of the tumor cell group (CT-26).

From the above experimental results, it can be seen that the activity of the penetrating peptide was selectively recovered in the tumor cell group, and thus the penetrating peptide-anticancer protein conjugate was introduced into the tumor cells so that it showed effective anticancer activity even at low concentration.

INDUSTRIAL APPLICABILITY

As described above, the target-activated cell/tissue-penetrating peptide-drug conjugate according to the present invention shows high safety, maximizes the effects of diagnosis and drug therapy through optimal targeting and can minimize side effects, unlike existing non-specific and non-selective peptide transporters. Accordingly, the present invention provides a pharmaceutical composition for diagnosis and treatment of disease, which comprises a target-activated cell/tissue-penetrating peptide-drug conjugate that is introduced specifically into target cells, thereby proposing an innovative technology for the diagnosis and treatment of disease.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A target-activated cell/tissue-penetrating peptide-drug conjugate for delivery of impermeable compounds, wherein said target-activated cell/tissue-penetrating peptide includes:
a protein transduction domain (PTD), wherein the protein transduction domain (PTD) consists of D-type or L-type amino acids, and contains any one or more amino acids selected from the group consisting of arginine, lysine and histidine in an amount of 70-80%, wherein the protein transduction domain (PTD) is low molecular weight protamine (LMWP);
a masking domain ionically bonded with the protein transduction domain (PTD), wherein the masking domain ionically bonded with the protein transduction domain (PTD) consists of D-type or L-type amino acids, and contains anionic amino acids in an amount of 70-100%, wherein the anionic amino acids include glutamic acid or aspartic acid, wherein the masking domain consists of 4-8 amino acids; and
a spacer connecting the protein transduction domain (PTD) with the masking domain and having a cleavage site specific for a target cell/tissue enzyme, wherein the spacer has a site which is cleaved by matrix metalloprotease (MMP), wherein the spacer consists of SEQ ID NO: 25 (PLGLAG),
wherein said target-activated cell/tissue-penetrating peptide-drug conjugate is prepared with a crosslinker selected from succinimidyl-4-[N-maleimidomethylcyclohexane-1-carboxy-[6-amidocaproate]] (SMCC) or its sulfonate (sulfo-SMCC).

2. The target-activated cell/tissue-penetrating peptide-drug conjugate according to claim 1, wherein the target-activated cell/tissue-penetrating peptide-drug conjugate comprises the drug which is conjugated at the protein transduction domain (PTD) of the target-activated cell/tissue-penetrating peptide.

3. The target-activated cell/tissue-penetrating peptide-drug conjugate according to claim 2, wherein the target-activated cell/tissue-penetrating peptide-drug conjugate comprises the drug which is conjugated at the protein transduction domain (PTD) by cysteine.

4. The target-activated cell/tissue-penetrating peptide-drug conjugate according to claim 1, wherein the drug is selected from the group consisting of anticancer agents, anticancer proteins, anti-inflammatory agents, anti-inflammatory proteins, immune enhancing proteins, bone resorption inhibitors, antisense oligonucleotides targeting the ribonucleic acid (RNA) of tumor or inflammatory disease proteins, and small interfering ribonucleic acids (siRNAs) targeting the RNA of tumor or inflammatory disease proteins.

5. The target-activated cell/tissue-penetrating peptide-drug conjugate according to claim 4, wherein the tumor or inflammatory disease proteins are selected from the group consisting of vascular endothelial growth factor (VEGF), B-cell leukemia/lymphoma 2 (BCL2), epidermal growth factor receptor (EGFR), human epidermal growth factor receptor 2 (HER2), Janus kinase (JAN), and phosphatidylinositol-3-kinase/Akt kinase (PI3-K/AKT).

6. A pharmaceutical composition comprising the target-activated cell/tissue-penetrating peptide-drug conjugate of claim 4.

* * * * *

UNITED STATES PATENT AND TRADEMARK OFFICE
CERTIFICATE OF CORRECTION

PATENT NO. : 8,796,219 B2
APPLICATION NO. : 13/202317
DATED : August 5, 2014
INVENTOR(S) : Yoon-Jeong Park et al.

Page 1 of 1

It is certified that error appears in the above-identified patent and that said Letters Patent is hereby corrected as shown below:

In the Specification

Column 9, lines 9 and 49: "(5 $\mu$g/M1)" should be – (5 µg/M$\ell$)

Signed and Sealed this
Twenty-eighth Day of October, 2014

Michelle K. Lee
*Deputy Director of the United States Patent and Trademark Office*